(12) United States Patent
Meron

(10) Patent No.: US 7,201,872 B2
(45) Date of Patent: Apr. 10, 2007

(54) SYSTEM AND METHOD FOR DETERMINING THE PRESENCE OF A SUBSTANCE IN-VIVO

(75) Inventor: Gavriel Meron, Petach Tikva (IL)

(73) Assignee: Given Imaging Ltd., Yoqneam (IL)

( * ) Notice: Subject to any disclaimer, the term of this patent is extended or adjusted under 35 U.S.C. 154(b) by 183 days.

(21) Appl. No.: 10/036,490

(22) Filed: Jan. 7, 2002

(65) Prior Publication Data

US 2002/0146368 A1    Oct. 10, 2002

Related U.S. Application Data

(63) Continuation of application No. 09/487,337, filed on Jan. 19, 2000, now abandoned.

(51) Int. Cl.
*G01N 21/00* (2006.01)
*C12M 3/00* (2006.01)

(52) U.S. Cl. .................. 422/57; 422/58; 435/287.1; 435/287.2; 435/287.9; 436/518; 436/164; 604/890.1; 604/891.1; 424/9.1

(58) Field of Classification Search ............ 435/4, 435/7.9, 1.92, 174, 176, 177, 180, 181, 287.1, 435/287.2, 287.7, 287.9, 288.7, 808; 436/63, 436/164, 169, 172, 518, 524, 527, 528, 532, 436/805, 811, 823; 424/9.1; 128/760, 769; 604/11, 19, 27, 891.1, 890.1, 67; 422/50, 422/55–58, 62, 68.1, 82.05, 119, 939
See application file for complete search history.

(56) References Cited

U.S. PATENT DOCUMENTS

| 3,971,362 A | 7/1976 | Pope et al. |
| 4,017,261 A | 4/1977 | Svoboda et al. |
| 4,038,485 A | 7/1977 | Johnston et al. |
| 4,239,040 A | 12/1980 | Hosoya et al. |
| 4,278,077 A | 7/1981 | Mizumoto |
| 4,337,222 A | 6/1982 | Kitajima et al. |
| 4,439,197 A | 3/1984 | Honda et al. |
| 4,689,621 A | 8/1987 | Kleinberg |

(Continued)

FOREIGN PATENT DOCUMENTS

| DE | 34 40 177 | 5/1986 |
| EP | 1 002 229 | 1/2004 |
| FR | 2 688 997 | 10/1993 |

(Continued)

OTHER PUBLICATIONS

The Radio Pill, Rowlands, et al., British Communications and Electronics, Aug. 1960, pp. 598-601.

(Continued)

*Primary Examiner*—Long V. Le
*Assistant Examiner*—Gary W. Counts
(74) *Attorney, Agent, or Firm*—Pearl Cohen Zedek Latzer LLP

(57) ABSTRACT

The present invention relates to a method and system for the in vivo determination of the presence and/or concentration of biological and/or chemical substances in body lumens. The system of the invention comprises a solid support, the support being inserted into a body lumen and having immobilized thereon at least one reactant capable of reacting with the substance resulting in an optical change; and a detecting unit, in communication with the support, capable of detecting a reaction resulting in an optical change between the reactant and the substance.

17 Claims, 21 Drawing Sheets

U.S. PATENT DOCUMENTS

| | | |
|---|---|---|
| 4,803,992 A | 2/1989 | Lemelson |
| 4,844,076 A | 7/1989 | Lesho et al. |
| 4,885,077 A | 12/1989 | Karakelle et al. |
| 4,920,045 A | 4/1990 | Okuda et al. |
| 5,042,486 A | 8/1991 | Pfeiler et al. |
| 5,081,040 A | 1/1992 | Patel et al. |
| 5,109,870 A | 5/1992 | Silny et al. |
| 5,114,864 A | 5/1992 | Walt |
| 5,211,165 A | 5/1993 | Dumoulin et al. |
| 5,252,494 A | 10/1993 | Walt |
| 5,279,607 A | 1/1994 | Schentag et al. |
| 5,306,623 A | 4/1994 | Kiser et al. |
| 5,330,427 A | 7/1994 | Weissenburger |
| 5,362,478 A | 11/1994 | Desai et al. |
| 5,385,846 A | 1/1995 | Kuhn et al. |
| 5,395,366 A | 3/1995 | D'Andrea et al. |
| 5,429,132 A | 7/1995 | Guy et al. |
| 5,443,701 A | 8/1995 | Willner et al. |
| 5,447,868 A | 9/1995 | Augurt |
| 5,460,969 A | 10/1995 | Fielder et al. |
| 5,479,935 A | 1/1996 | Essen-Moller |
| 5,490,969 A | 2/1996 | Bewlay et al. |
| 5,558,640 A | 9/1996 | Pfeiler et al. |
| 5,563,071 A | 10/1996 | Augurt |
| 5,604,531 A | 2/1997 | Iddan et al. |
| 5,762,770 A | 6/1998 | Pritchard et al. |
| 5,800,350 A | 9/1998 | Coppleson et al. |
| 5,814,525 A | 9/1998 | Renschler et al. |
| 5,819,736 A | 10/1998 | Avny et al. |
| 5,833,602 A | 11/1998 | Osemwota |
| 5,833,603 A | 11/1998 | Kovacs et al. |
| 5,837,196 A | 11/1998 | Pinkel et al. |
| 5,853,005 A | 12/1998 | Scanlon |
| 5,892,144 A | 4/1999 | Meller et al. |
| 5,913,820 A | 6/1999 | Bladen et al. |
| 5,916,176 A | 6/1999 | Caillouette |
| 5,932,480 A | 8/1999 | Maruo et al. |
| 5,968,765 A | 10/1999 | Grage et al. |
| 5,993,378 A | 11/1999 | Lemelson |
| 6,099,482 A | 8/2000 | Brune et al. |
| 6,149,581 A | 11/2000 | Klingenstein |
| 6,162,469 A * | 12/2000 | Atarashi et al. ............ 424/617 |
| 6,240,312 B1 | 5/2001 | Alfano et al. |
| 6,285,897 B1 | 9/2001 | Kilcoyne et al. |
| 6,330,464 B1 | 12/2001 | Colvin, Jr. et al. |
| 6,369,812 B1 | 4/2002 | Iyriboz et al. |
| 6,395,562 B1 | 5/2002 | Hammock et al. |
| 6,475,145 B1 | 11/2002 | Baylor |
| 6,488,694 B1 | 12/2002 | Lau et al. |
| 2001/0035902 A1 | 11/2001 | Iddan et al. |
| 2002/0001695 A1 | 1/2002 | Tajima et al. |
| 2002/0015952 A1 | 2/2002 | Anderson et al. |
| 2002/0103417 A1 | 8/2002 | Gazdzinski |
| 2002/0173718 A1 | 11/2002 | Frisch et al. |
| 2002/0177779 A1 | 11/2002 | Adler et al. |
| 2002/0198439 A1 | 12/2002 | Mizuno |
| 2003/0020810 A1 | 1/2003 | Takizawa et al. |
| 2003/0023150 A1 | 1/2003 | Yokoi et al. |

FOREIGN PATENT DOCUMENTS

| | | |
|---|---|---|
| JP | 4109927 | 4/1992 |
| JP | 5015515 | 1/1993 |
| JP | 6285044 | 10/1994 |
| JP | 7111985 | 5/1995 |
| JP | 2002-010990 | 12/2001 |
| WO | WO 97/45720 | 12/1997 |
| WO | WO 98/07366 | 2/1998 |
| WO | WO 99/11754 | 3/1999 |
| WO | WO 99/32028 | 7/1999 |
| WO | WO 00/22975 | 4/2000 |
| WO | WO 01/08548 | 2/2001 |
| WO | WO 02/55984 | 7/2002 |

OTHER PUBLICATIONS

Wellesley company sends body montiors into space—Crum, Apr. 1998.

Wireless transmission of a color television moving image from the stomach using a miniature CCD camera, light source and microwave transmitter Swain CP, Gong F, Mills TN. Gastrointest Endosc 1997;45:AB40.

In vitro leucocyte adhesion to modified polyurethane surfaces—Bruil, Biomaterials 1992. vol. 13, No. 13.

Medical Diagnosis Reagents, vol. 16.

Heidelberger Kapsel—ein Kleinstsender fur die pH-Messung im Magen, Lange, et al., Telefunken-Zeitung, Jg 36 (1963) Heft 5, pp. 265-270.

Video Camera to "Take" -RF System Lab, Dec. 25, 2001.

"New Smart Plastic has Good Memory" -Turke, Europeon Medical Device Manufacturer, devicelink.com, Sept. 2001.

* cited by examiner

SYSTEM AND METHOD FOR DETERMINING THE PRESENCE OF A SUBSTANCE IN-VIVO

PRIOR APPLICATION

This application is a continuation of prior U.S. application Ser. No. 09/487,337 filed 19 Jan. 2000 now abandoned and entitled "A System For Detecting Of Substances".

FIELD OF THE INVENTION

The present invention generally relates to a method and system for the detection of biological and/or chemical substances in vivo. More specifically, the present invention relates to a method and system for determining the presence and/or concentration of biological and/or chemical substances in body lumens.

BACKGROUND OF THE INVENTION

An atypical concentration or presence of substances in body fluids is indicative of the biological condition of the body. For example, the presence of HGC hormone in the blood of a human is characteristic of pregnancy. The presence of certain compounds or cells in the blood stream or in other body fluids characterizes pathologies. For example, an elevated level of sugar in the blood indicates an impaired function of certain organs. The presence of elevated concentrations of red blood cells in the gastrointestinal (GI) tract indicates different pathologies, depending on the location of the bleeding along the GI tract.

Early detection and identification of these biological or chemical substances is critical for correctly diagnosing and treating the various body conditions.

Medical detection kits are usually based on testing body fluid samples for the presence of a suspected substance i.e. In Vitro Diagnostics (IVD). This method of detection does not easily enable the localization or identification of the origin of an abnormally occurring substance. In many instances localizing an abnormally occurring substance in a body lumen greatly contributes to the identification of a pathology, and thus contributes to the facile treatment of the identified pathology. For example, bleeding in the stomach may indicate an ulcer while bleeding in the small intestine may indicate the presence of a tumor. The commonly used chemical methods for detecting blood in the GI tract do not enable the identification of the origin of the bleeding and further testing must be carried out to determine the type of pathology.

Detection of bleeding in the GI tract is possible by endoscope, however it is limited to the upper or lower gastrointestinal tract. Thus bleeding in the small intestine is not easily detected by endoscopy.

Parameters such as temperature, pH and pressure in the GI tract can be monitored by swallowable telemetry pills, such as the Heidelberg Capsule. For monitoring the gastric pH the Heidelberg Capsule, which is a miniaturized radio transmitter, comprises a pH measuring cell comprising two electrodes, one of which is in direct contact with the gastric fluid. The two electrodes are separated by a membrane permeable to ions (base battery), whereas pH changes alter the output voltages of the base battery which in turn effects the frequency of the capsule radio transmitter emission.

SUMMARY OF THE INVENTION

The present invention relates to a method and system for the in vivo determination of the presence and/or concentration of biological and/or chemical substances in body lumens. The method and system of the present invention enable to optically monitor the environment in a body lumen as far as the presence or concentration of a biological or chemical substance is concerned, such that the presence of a substance or a change in the concentration of a substance is immediately optically detected and can be localized to a specific place in the body lumen.

The system of the invention comprises a solid support, the support being inserted into a body lumen and having immobilized thereon at least one reactant capable of reacting with the substance resulting in an optical change; and a detecting unit, in communication with the support, capable of detecting a reaction resulting in an optical change between the reactant and the substance.

The support may be, for example, nylon, glass, plastic or any support capable of immobilizing thereon a reactant.

The reactant is capable of being immobilized onto the support and is capable of reacting with substances in body lumens whereas the reaction results in an optical change. The reactant may be a poly electrolyte such as poly acrylic acid (PAA), poly aspartic acid, poly glutamic acid or cellulose acetic acid. The reactant may further be a protein immobilized onto the support either directly or via a bridging group, such as a thrombin molecule immobilized onto a pretreated support or antibodies immobilized onto the support through a suitable mediator group.

The substance is any ion, radical or compound composite contained in body lumens, such as blood components.

The support can be attached to or can be an integral part of a medical device that can be inserted into body lumens, such as a stent, needle, endoscope or a swallowable capsule.

The present invention further relates to a method for determining in vivo the presence and/or concentration of a biological and/or chemical substance in a body lumen. The method comprises the steps of a) inserting into a body lumen a solid support, said support having immobilized thereon at least one reactant capable of reacting with the substance resulting in an optical change and said support being in communication with a detecting unit that is capable of detecting a reaction resulting in an optical change between the reactant and the substance; and b) receiving information from the detecting unit.

The present invention further relates to a swallowable capsule comprising the system of the invention.

The present invention yet further relates to a diagnostic device for the detection of blood in body lumens comprising a plastic support having immobilized thereon a reactant capable of reacting with blood or blood components such that the reaction results in an optical change.

In one embodiment of the invention there is provided a swallowable capsule which includes a camera system, an optical system for imaging an area of interest onto the camera system and a transmitter which transmits the video output of the camera system. The swallowable capsule passes through the entire digestive tract operating as an autonomous video endoscope. The GI tract is imaged through the capsule's transparent optical window onto which poly acrylic acid molecules are immobilized. The reaction of blood components, if blood is present in the GI tract, with the poly acrylic acid molecules, is optically detectable and is transmitted with the video output such that the presence of blood is identified and the bleeding is localized in the GI tract while the capsule is still on site.

BRIEF DESCRIPTION OF THE DRAWINGS

The present invention will be understood and appreciated more fully from the following detailed description taken in conjunction with the appended drawings in which:

FIGS. 4B–4E show the absorption spectra of the support in a blood solution obtained at 90 seconds, 120 seconds, 150 seconds and 180 seconds respectively;

FIGS. 5B–5F show the spectra obtained at 10 seconds, 30 seconds, 45 seconds, 60 seconds and 90 seconds respectively;

FIGS. 6B–6F show the spectra obtained at 30 seconds, 60 seconds, 90 seconds, 120 seconds and 150 seconds respectively;

DETAILED DESCRIPTION OF THE INVENTION

The system and method of the present invention are utilized for the determination of the presence and/or concentration of biological and/or chemical substances in vivo. The method and system of the invention further enable to locate and localize an atypical substance or substance concentration in a body lumen.

Figure 1:
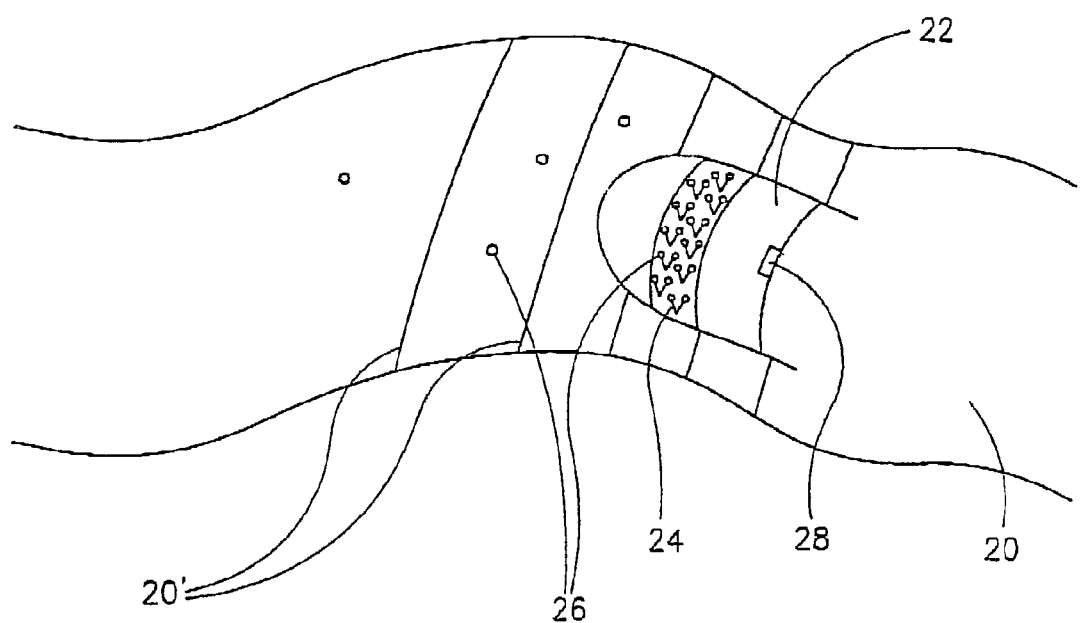
FIG. 1 is a schematic presentation of the system according to the invention.

Reference is made to FIG. 1 in which the system of the invention is schematically presented. The system comprises a solid support 22 which is coated with a band of reactant 24 layer and which is inserted into a body lumen 20 such that the reactant layer is immersed in the body lumen fluids 20' (diagonal stripes) and is in contact with the substances 26 contained in the body lumen fluids. The contact between the reactant and the substances results in a reaction which is optically detected and reported by the detecting unit 28.

The substance may be, for example, an ion, radical or compound composite and the reaction between the reactant and support may result in the deposition or binding of the substance 26 to the reactant 24, whereas the deposition or binding may further result in a change in the optical density of the support, in an electrochemical change resulting in a change of color on the support, in the transmission of light through the support, etc.

The chemical nature of the reaction ensures immediate results. Due to the immediate results of the reaction information can be immediately reported such that diagnostics and therapeutics are possible while the system is still on site.

Furthermore, the reaction between the reactant and substance is proportional to the concentration of the substance such that qualitative and quantitative results are obtained. Furthermore, a plurality of substance sources can be detected and identified unlike many IVD tests (pregnancy, sugar or protein in urine etc.) which do not respond to a subsequent exposure to the substance they detect. Thus, for example, not only can blood in the GI tract be detected but all sources of bleeding along the GI tract can be identified and localized.

The detecting unit 28 may be any unit capable of optically detecting and reporting the optical change brought about by the reaction. A suitable detecting unit may be the human eye, any suitable optical mechanical detecting unit or any suitable imaging device.

The support may be in communication with a monitoring unit that is capable of locating it in the body lumen. The monitoring unit may comprise a reception system that is operable with a transmitting unit that is also in communication with the support. The reception system is capable of receiving transmitted output from said transmitting unit thereby locating the support along a pre prepared map of the lumen. Thus, results can be reported to an operator outside the body. Locating a device such as the system of the invention is described in U.S. Pat. No. 5,604,531. U.S. Pat. No. 5,604,531, which is assigned to Given Imaging Ltd., is hereby incorporated by reference.

The immobilization of the reactant to the support depends on the specific characteristics of both reactant and support. The reactant may be applied directly to the support such as in the immobilizing of poly electrolytes onto the support. In this case different forces may be involved in the immobilization of the reactant to the support, such as electrostatic interactions, hydrogen bonding or hydrophilic interactions. The reactant may be applied onto a modified support, such as in the immobilization of thrombin molecules to a pretreated support or the reactant may be immobilized to the support via a bridging group such as in the immobilization of antibodies to the support through a suitable mediator group. The immobilization of the reactant to the support will be further described and illustrated by the following examples and experiments.

EXAMPLE 1

Figure 2:
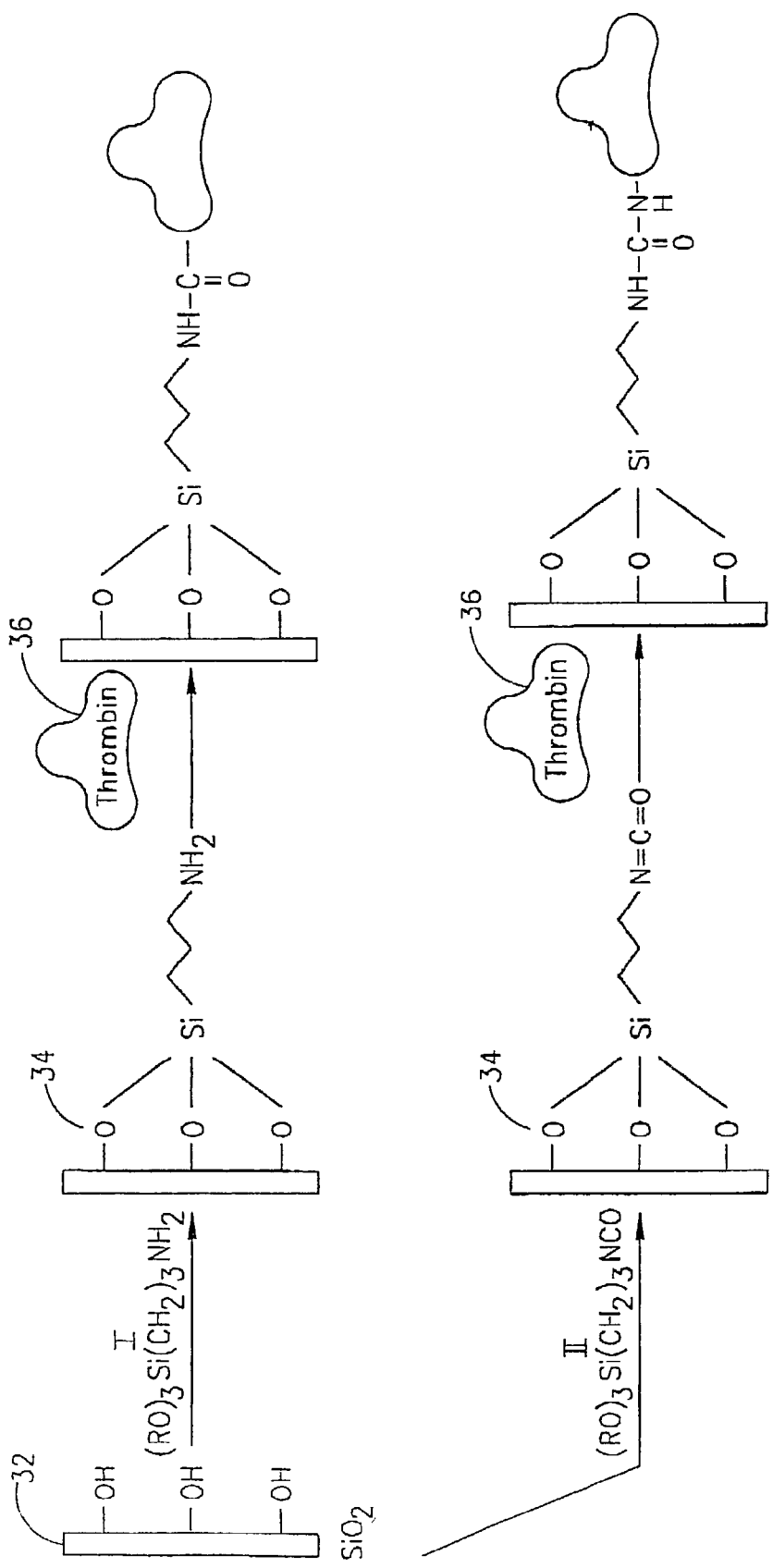
FIG. 2 is a schematic presentation of the process for the modification and functionalization of a support according to an embodiment of the invention.

As shown in FIG. 2, a glass or quartz support 32 is modified with a functionalized siloxane, such as compounds I or II. The modified support comprises a silylated monolayer 34 to which suitable compounds or molecules might be attached and immobilized. In FIG. 2 an exemplary protein molecule 36 is shown, namely a thrombin molecule. The immobilized protein 36 can now act as a reactant to react with substances. Thrombin is a plasma protein that is involved in blood clotting, specifically by converting the plasma protein fibrinogen into fibrin, the insoluble fibrous protein that holds blood clots together. This affinity between thrombin, the reactant, and componenets of the blood plasma, render thrombin a specific and effective blood detector. Thrombin induces deposition of fibrin onto the support The modified support is mounted on a structure which also includes a light source for illuminating through the coated support and an imaging device for capturing visual information obtained through the coated support. In the presence of blood, fibrin will be deposited onto the support consequently darkening any picture captured by the imaging device.

This structure can be tested for its durability and functionality as a detector of blood in a flow system through which buffer solutions comprising different concentrations of blood are injected. The effect on the light intensity as captured by the imaging device can be recorded. The coated support is also treated with acidic solutions having a pH in the range of 1.5 to 2, to examine possible effects of internal lumen (such as the stomach) acidity on the coating.

EXAMPLE 2

Figure 3:
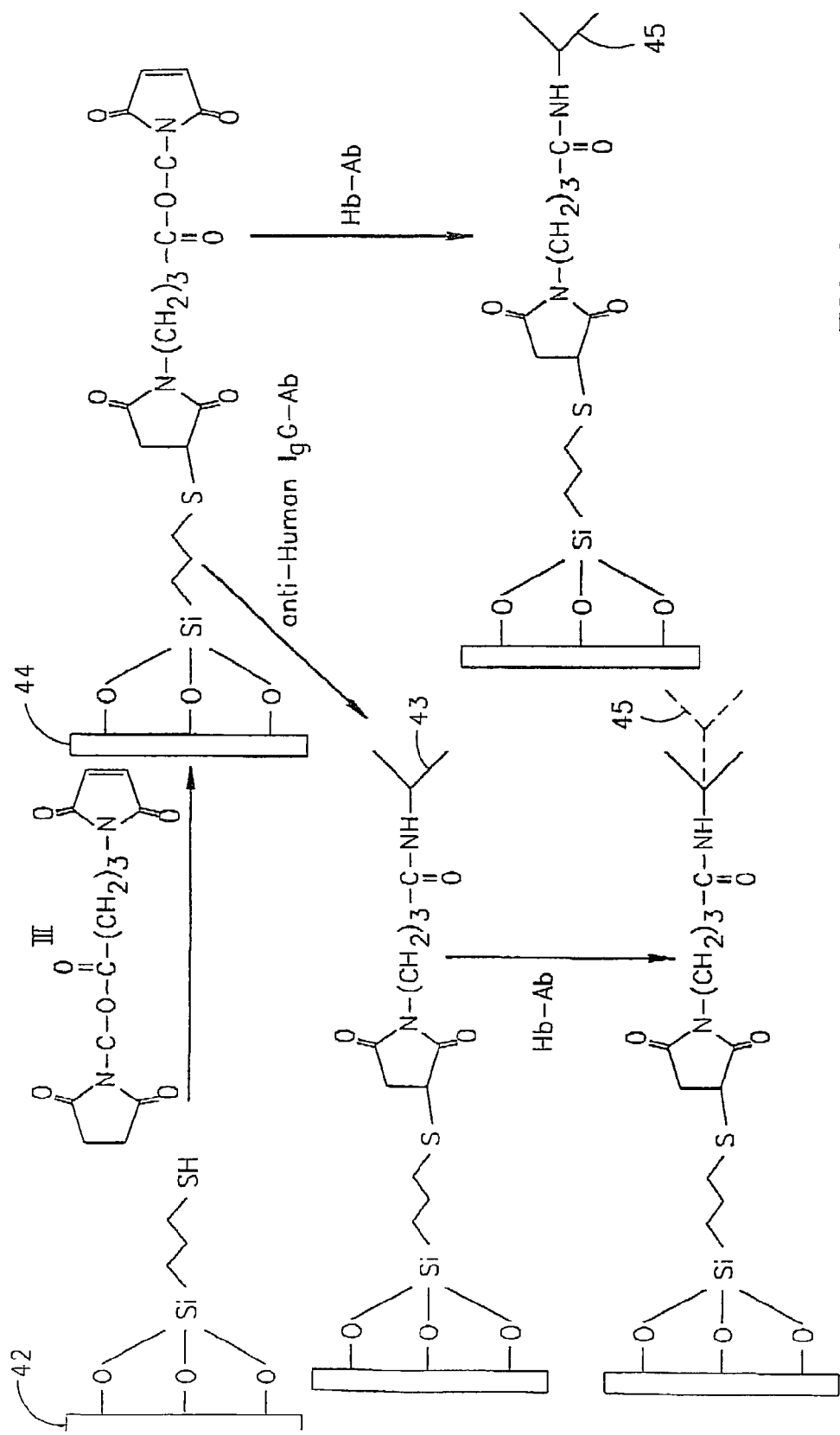
FIG. 3 is a schematic presentation of the process for the modification and functionalization of a support according to another embodiment of the invention.
Figure 4:
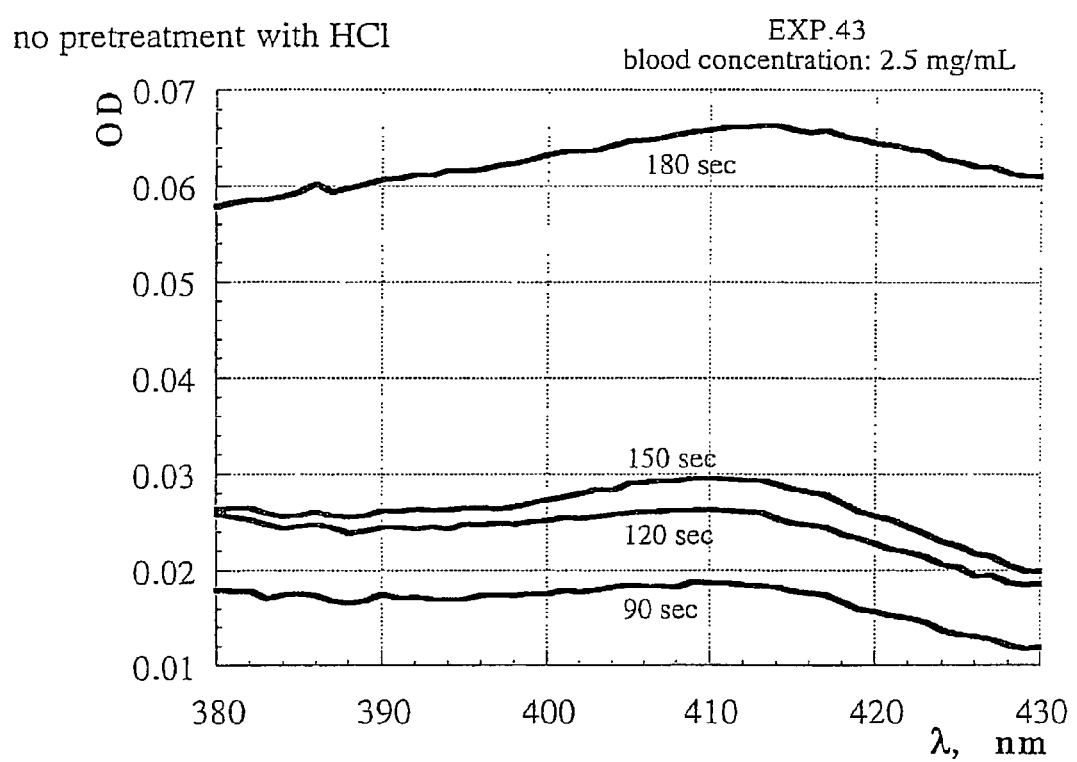
FIGS. 4A–E show the spectra obtained for blood solutions at a concentration of 2.5 mg/ml, with no HCI (2M) pretreatment.
Figure 4B:
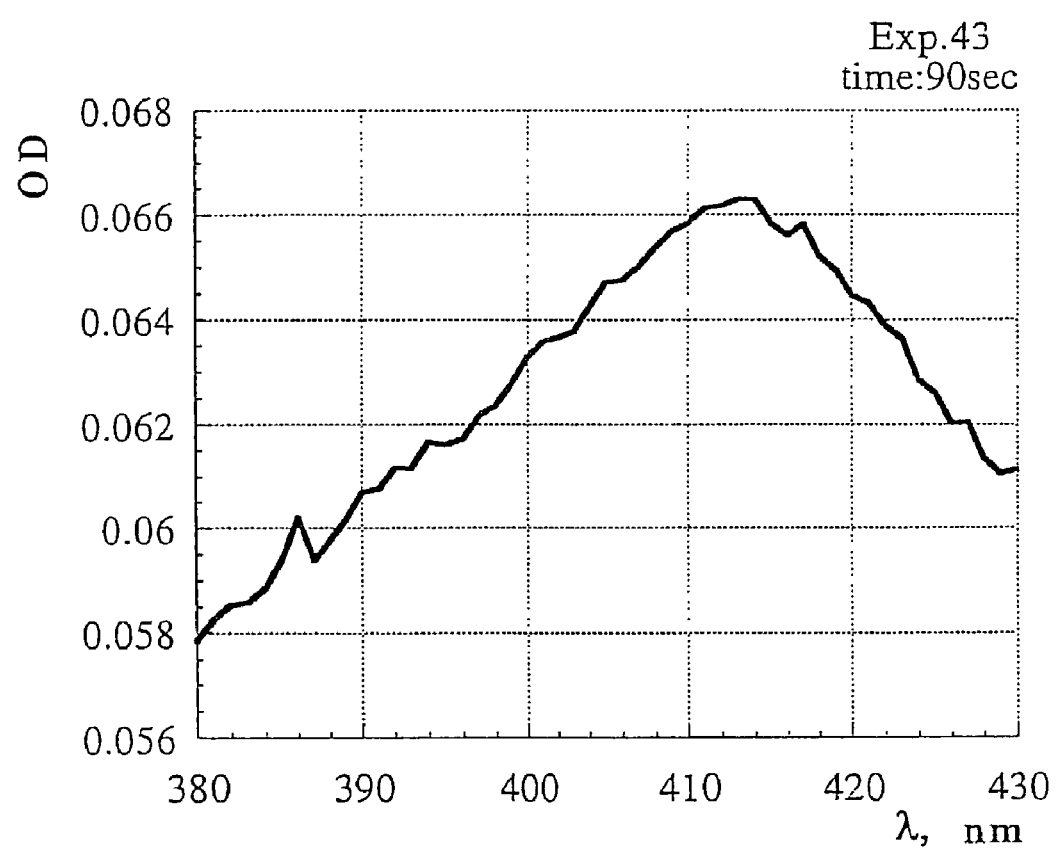
Figure 4C:
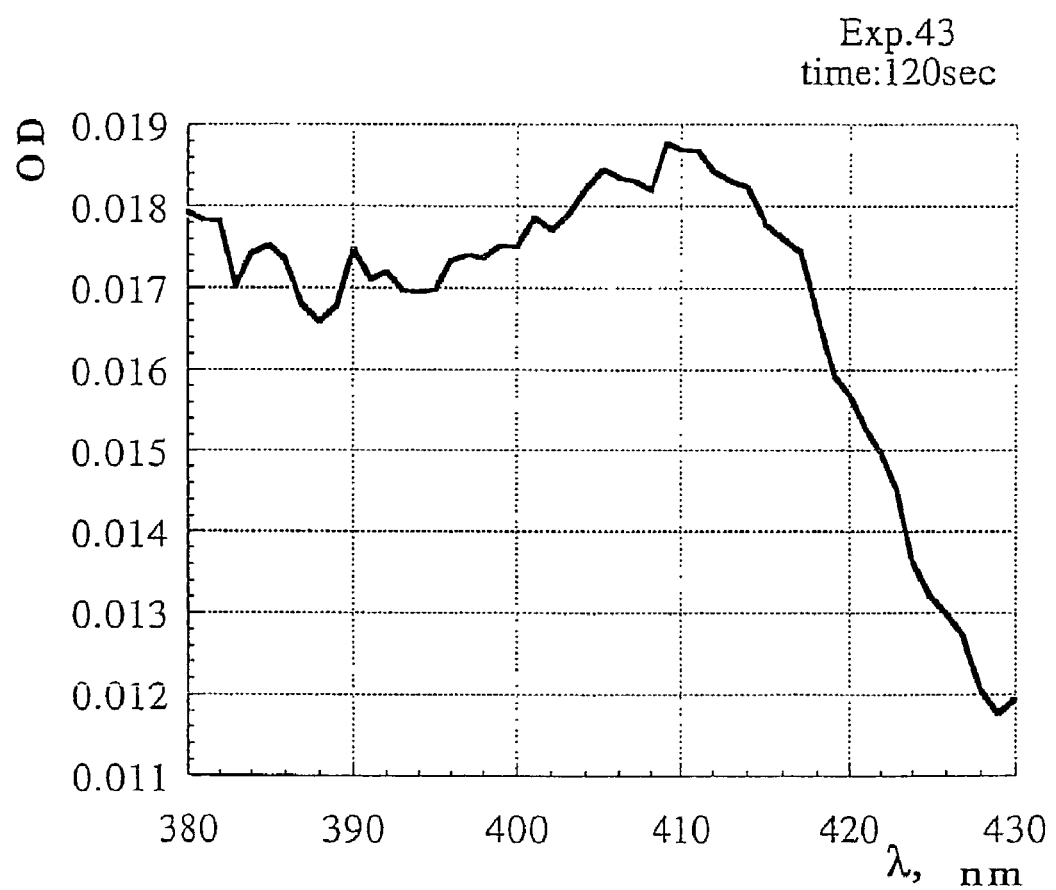
Figure 4D:
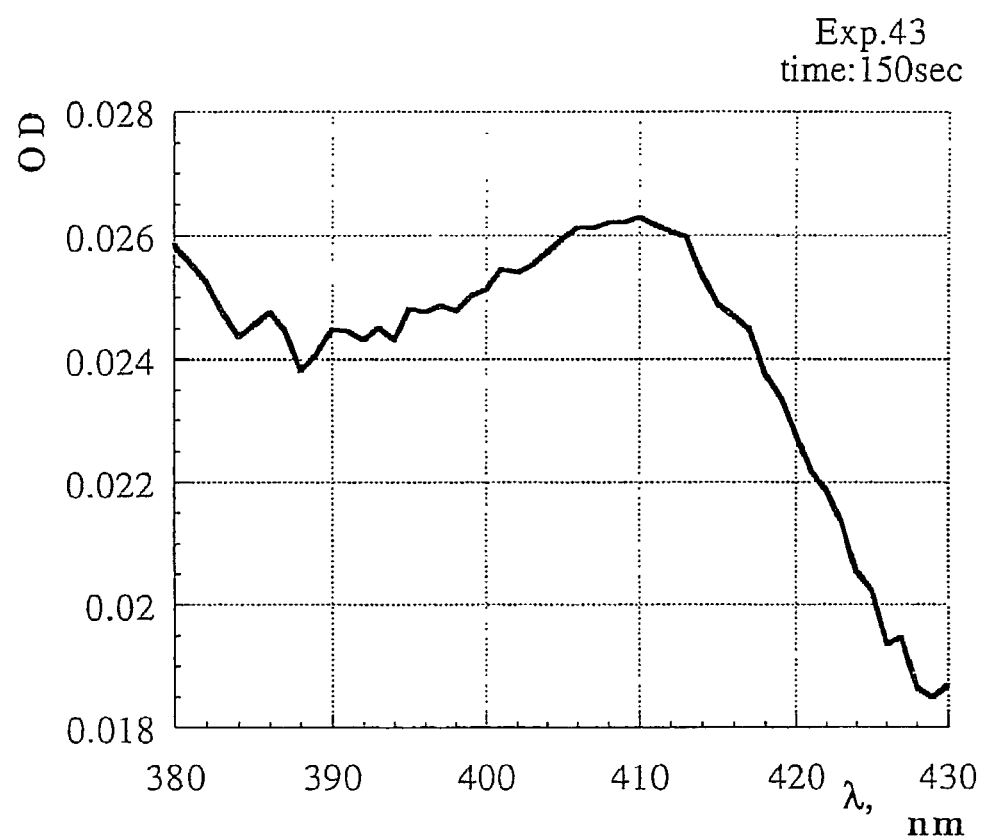
Figure 4E:
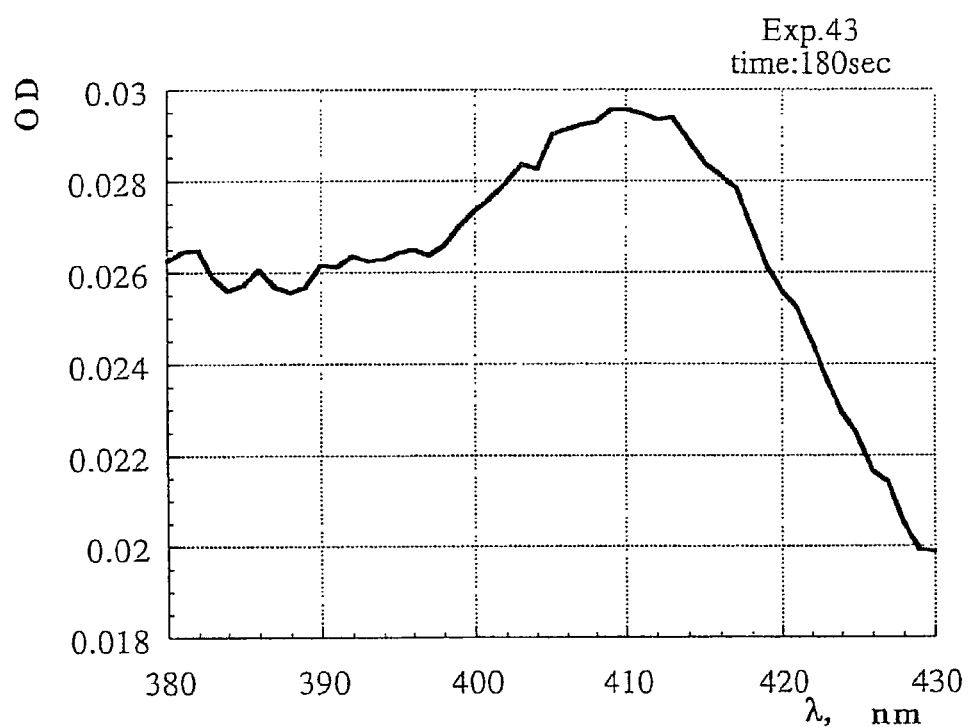
Figure 5A:
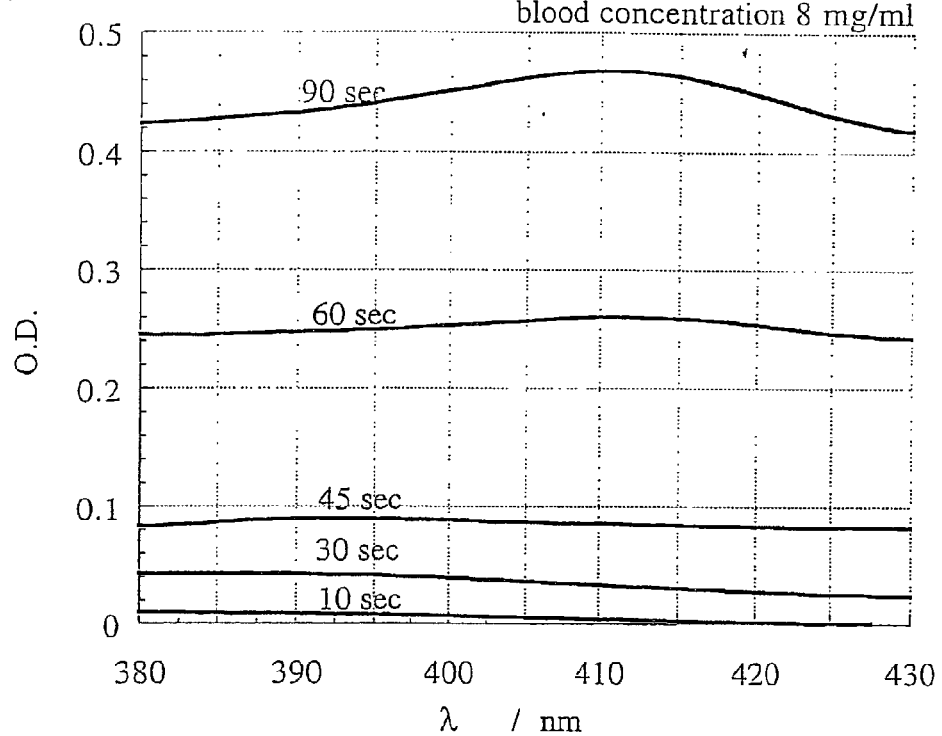
FIGS. 5A–F show the spectra obtained for blood solutions at a concentration of 8 mg/ml, with no HCI (2M) pretreatment.
Figure 5B:
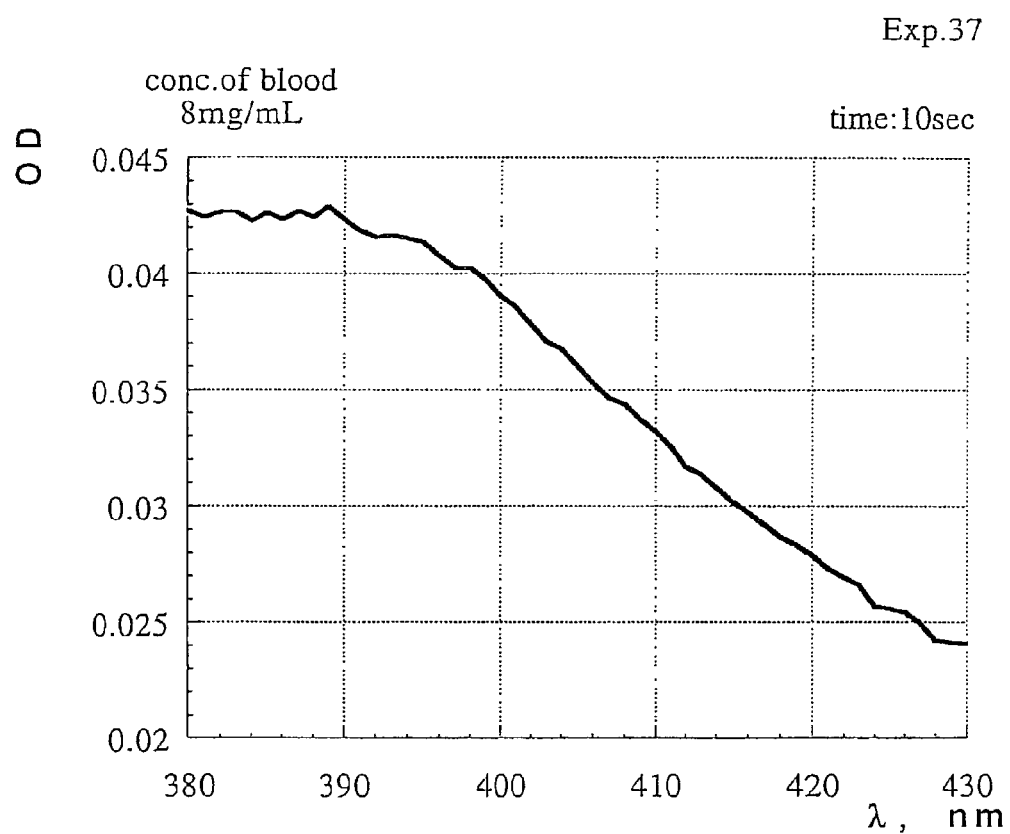
Figure 5C:
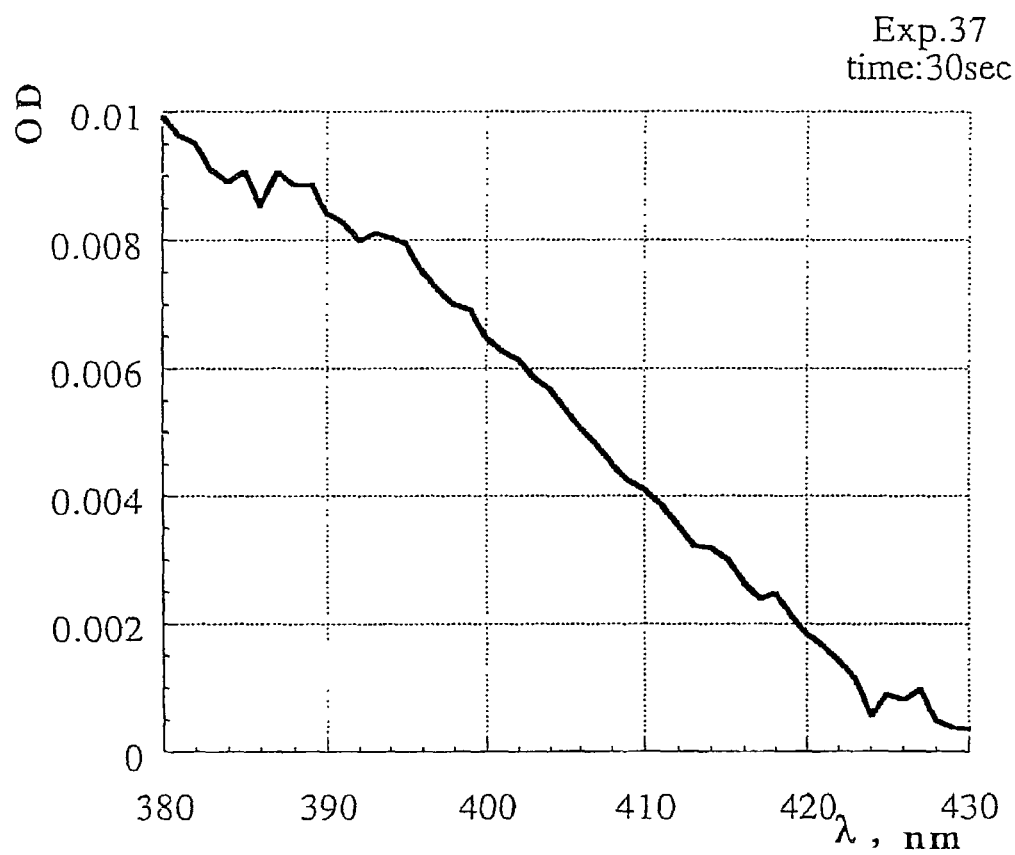
Figure 5D:
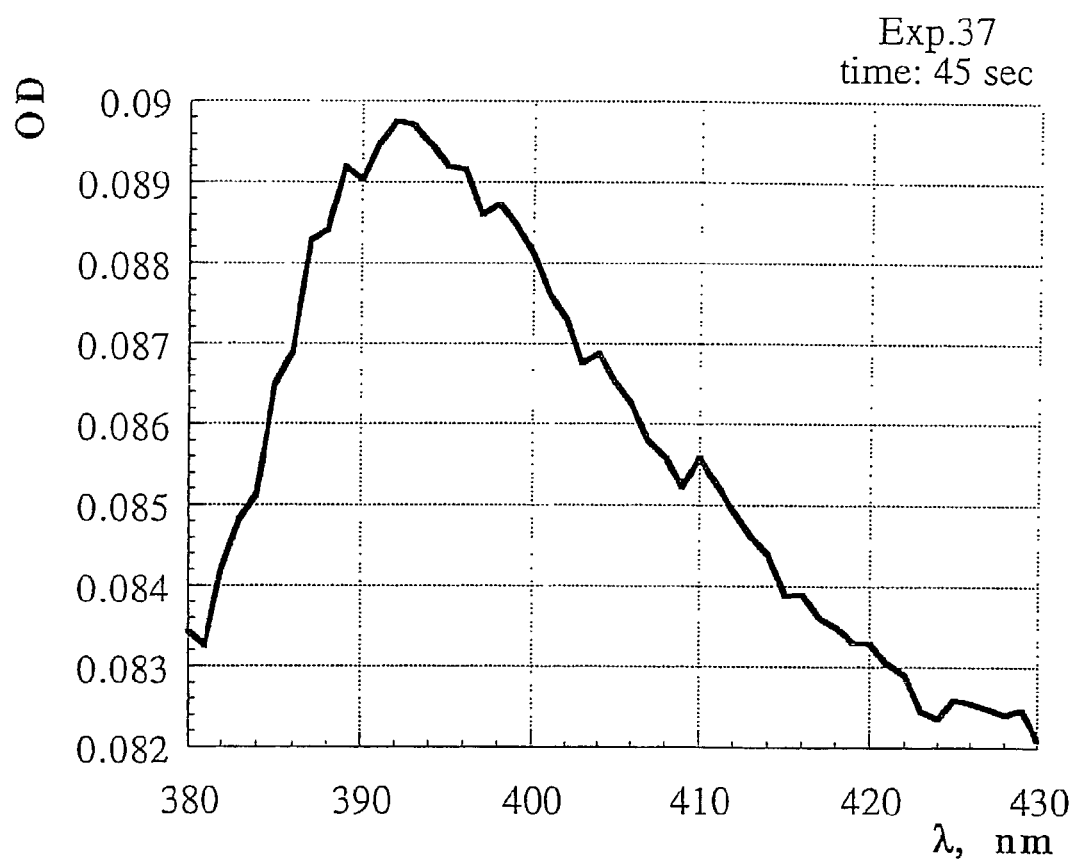
Figure 5E:
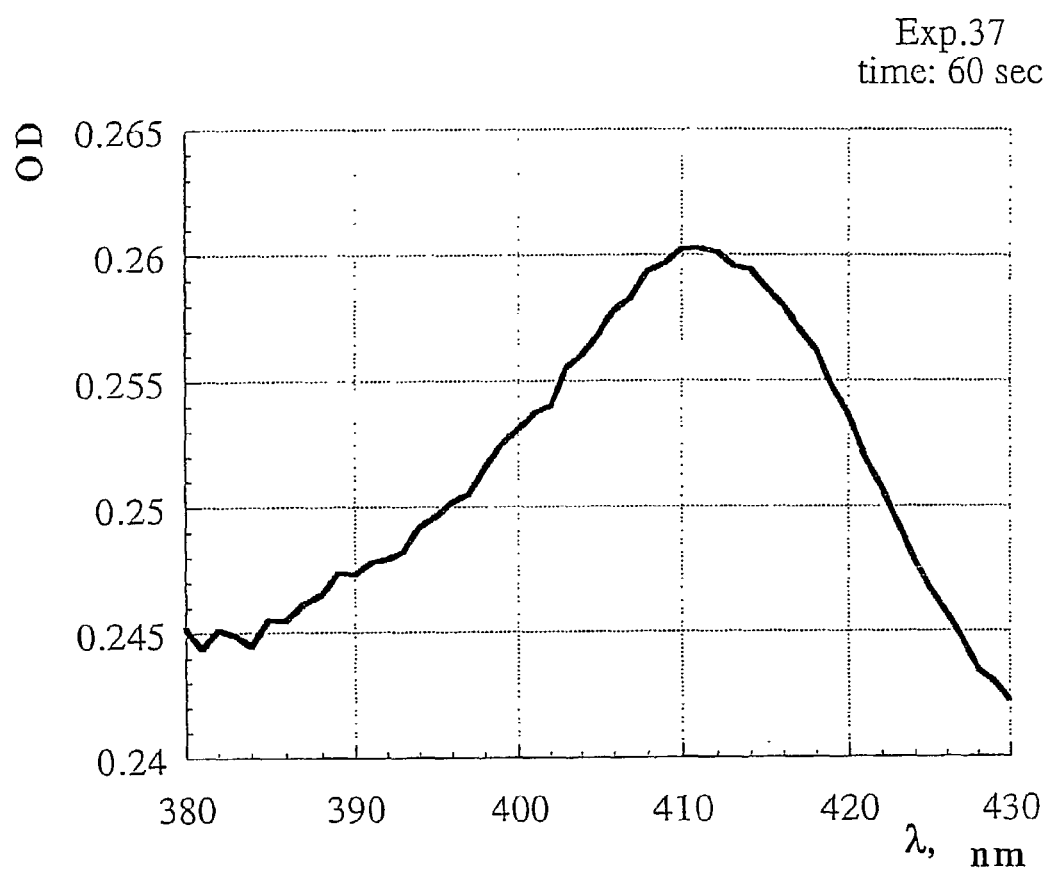
Figure 5F:
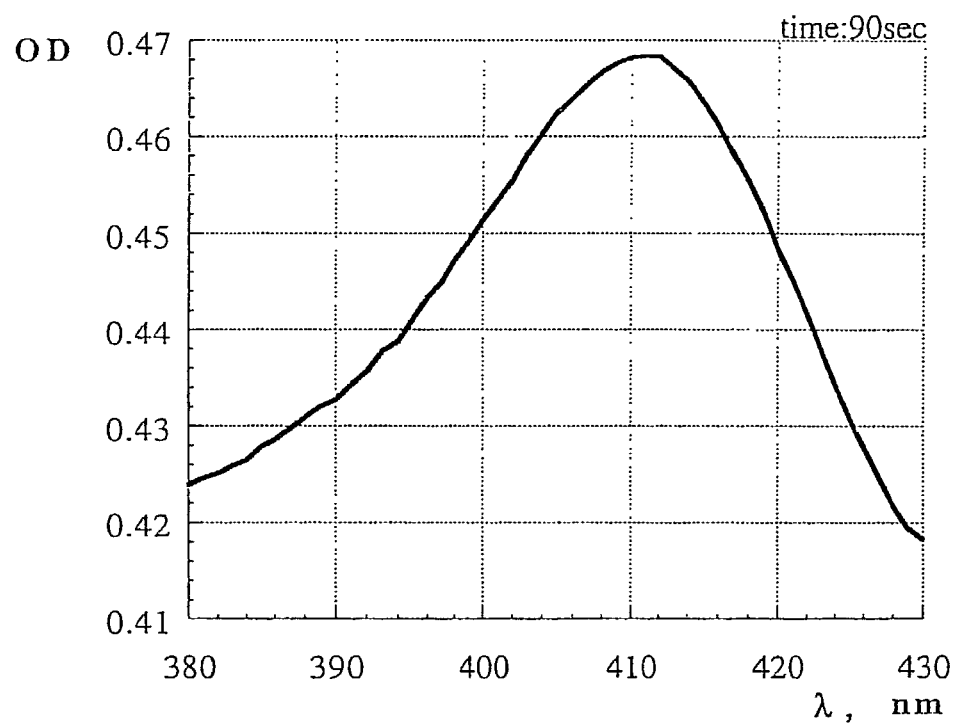
Figure 6A:
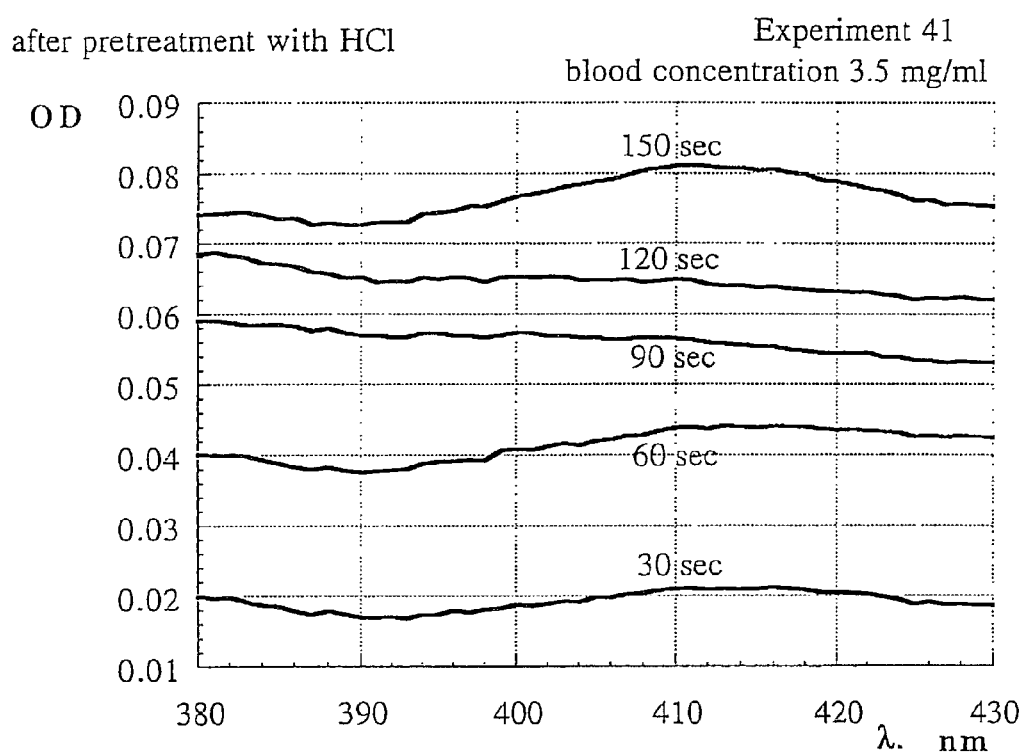
FIGS. 6A–F show the spectra obtained for blood solutions at a concentration of 3.5 mg/ml, with HCI pretreatment.
Figure 6B:
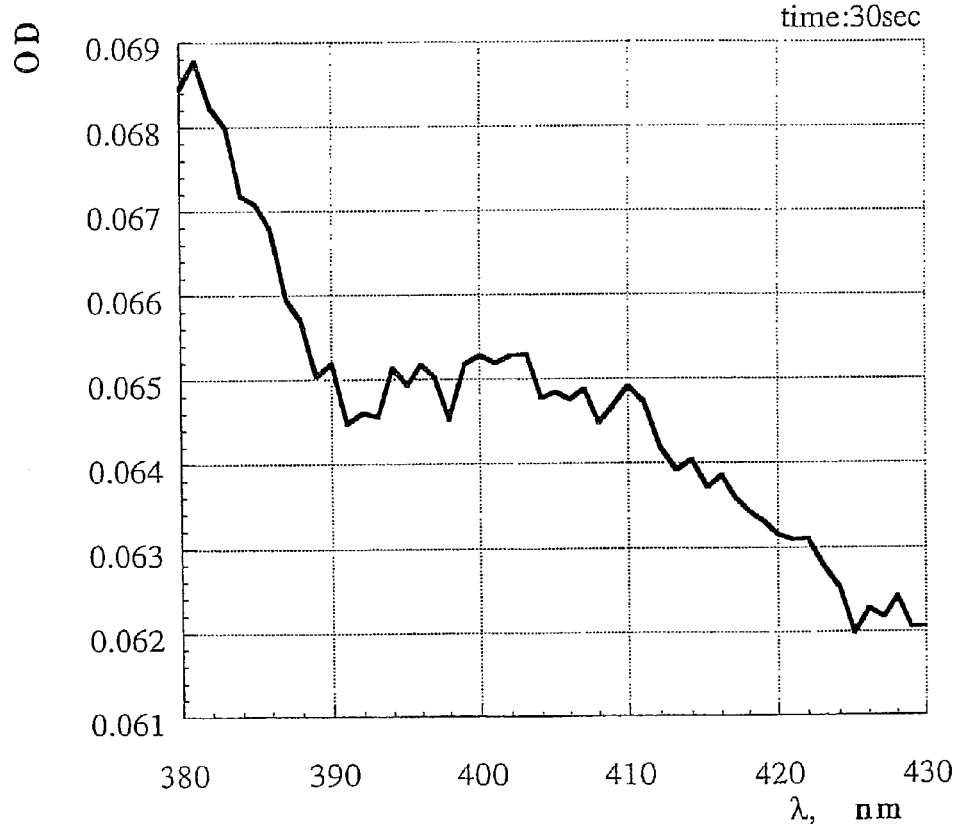
Figure 6C:
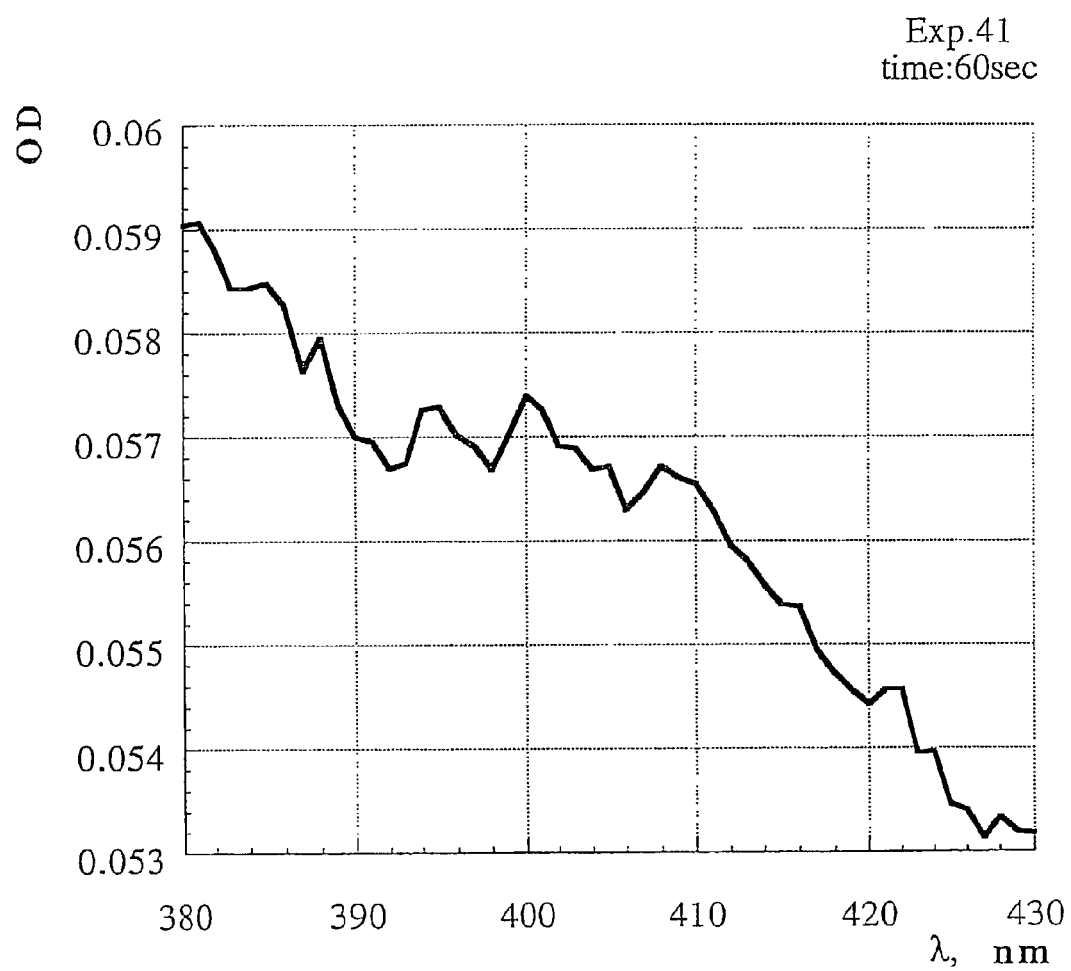
Figure 6D:
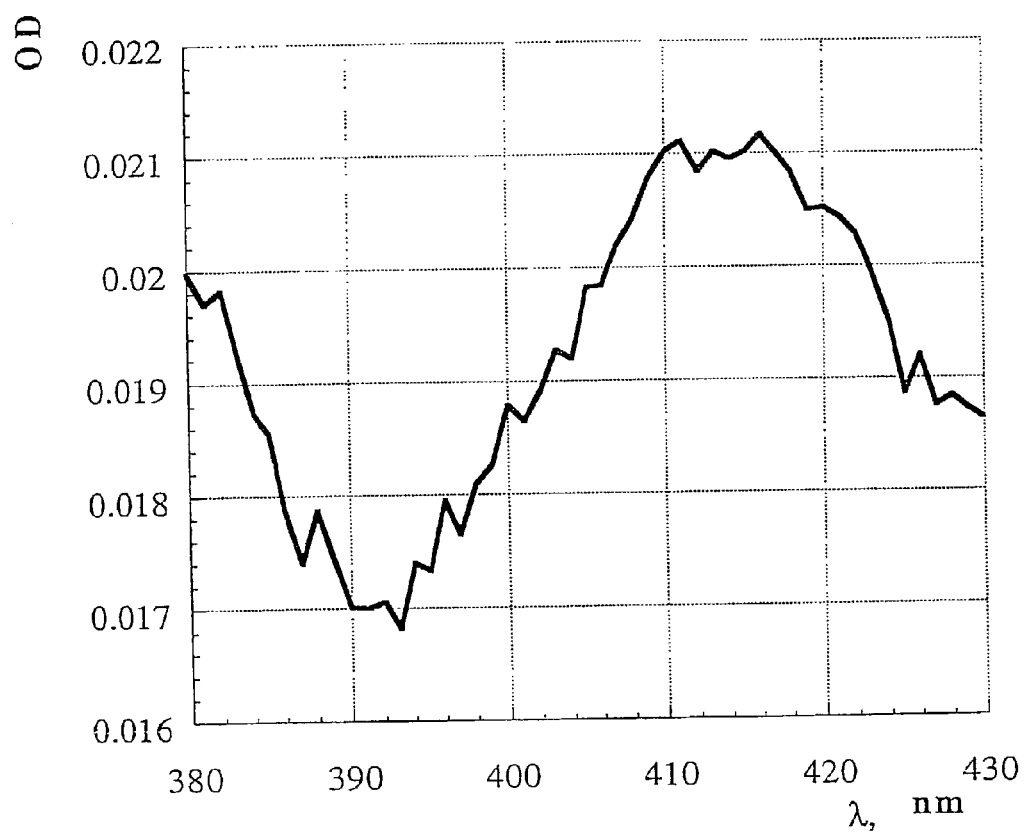
Figure 6E:
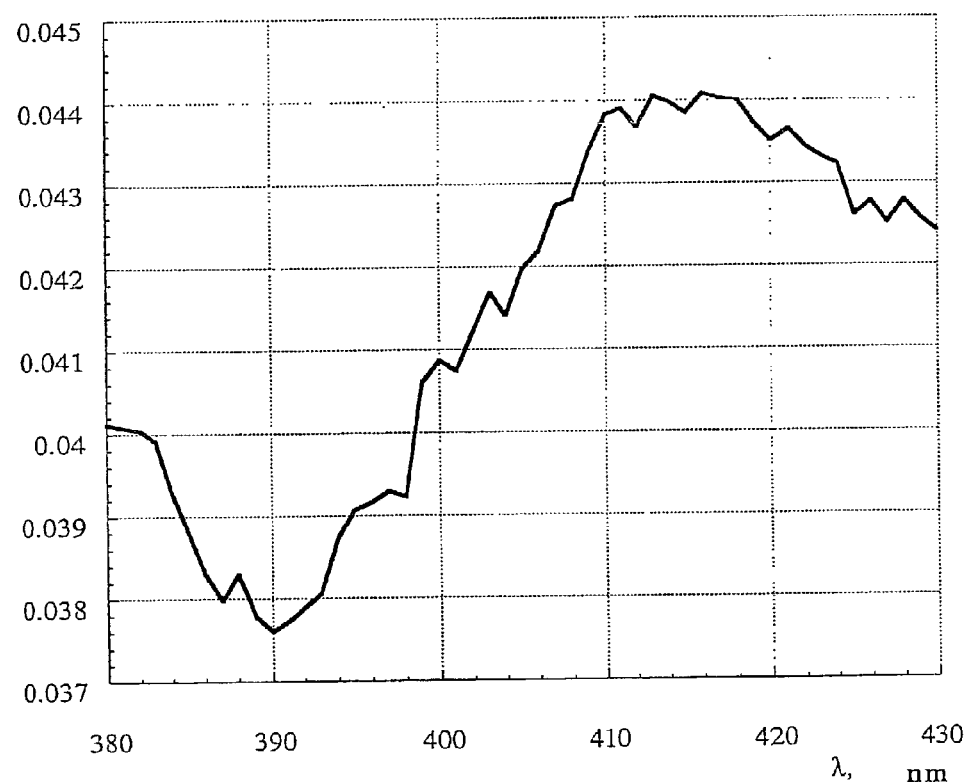
Figure 6F:
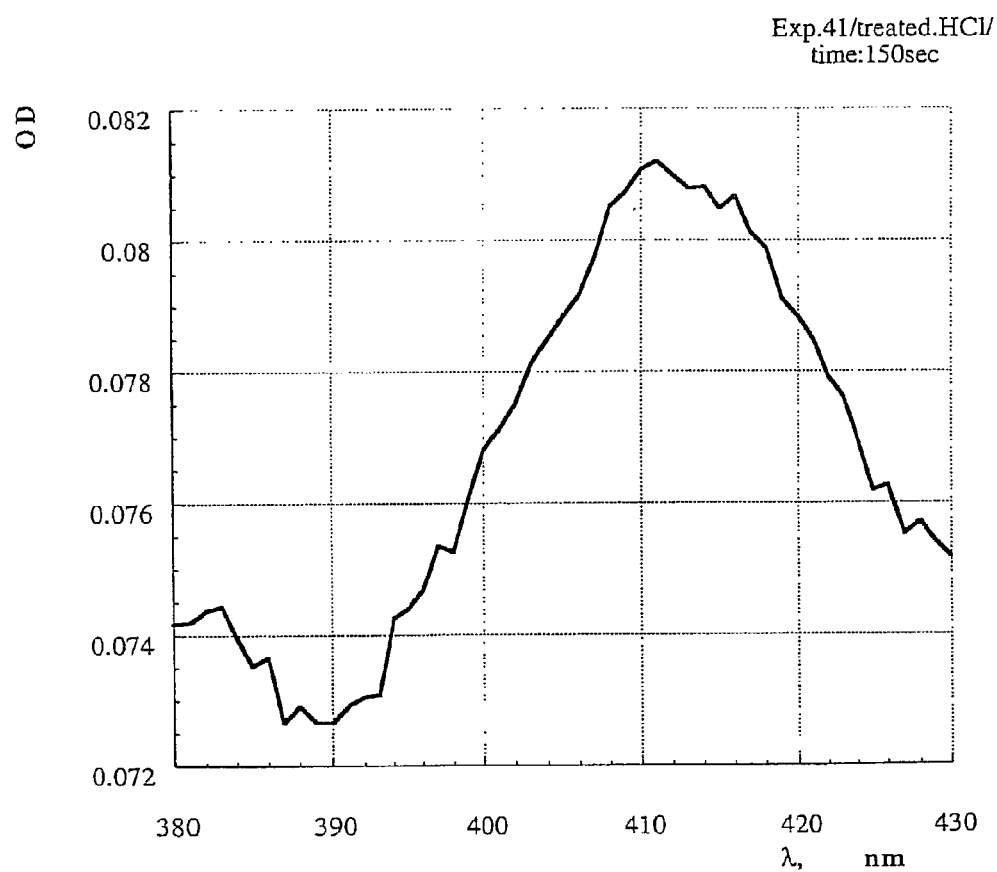

As shown in FIG. 3, a silylated glass or quartz support 42 is treated with compounds represented by compound III, resulting in a support having attached thereon a mediator group 44. Suitable compounds or molecules, represented by antibodies such as anti-Human IgG antibody 43 or Hemoglobin (Hb) antibody 45 are attached and immobilized to the mediator group. The immobilized Hb antibody, which can be attached to the mediator group or attached to the anti-Human IgG antibody 43, will induce the deposition of hemoglobin, the oxygen binding protein of red blood cells. Since hemoglobin absorbs blue light a change of color of the support is expected in the presence of blood.

The thus modified support is mounted onto a structure as described in Example 1 and the structure can be tested in a flow system as above.

EXAMPLE 3

A support made of a plastic such as isoplast is coated with poly electrolytes such as poly aspartic acid, poly glutamic acid, cellulose acetic acid or poly acrylic acid (PAA). The poly electrolytes are immobilized onto the support through electrostatic interactions, hydrogen bonding and hydrophilic interactions. It was found, for example, that a PAA coating induces stable deposition of hemoglobin.

Plates of isoplast (4 cm×4cm) were cleaned with a detergent solution, rinsed with a large amount of water (ultrapure) and then dried. 20% (w/w) aqueous solutions of PAA (M.W. 250,000) were used for the coating of the isoplast plates' surface. 0.7–0.8 ml of a PAA aqueous solution were spread onto a dry clean surface of an isoplast plate. After drying (by water evaporation) the coating's weight was approximately 0.01 gr (5–6 mg/cm$^{-2}$). Phosphate buffer solution (PBS) comprising 1.345 gr $Na_2HPO_4$, 0.125 gr $NaH_2PO_4$ and 5.171 gr KCl in 500 ml water, pH adjusted to 7.2, was used in the experiment.

EXPERIMENT—Blood Deposition on Isoplast Coated Plates

Blood samples obtained from different donors were diluted with PBS in a volumetric flask to obtain blood solutions at varying concentrations ranging from 2.5 to 25 mg/ml. A fresh blood sample from each donor was prepared each time just prior to the measurements.

Spectral measurements of the isoplast plates, before and after deposition of the blood were preformed using a UVI-CON-860 spectrophotometer in the range of 380 to 430 nm.

The process of blood coagulation on the modified isoplast plate surface was observed visually, by eye, as the formation of a brown-reddish percipitant, and by using a spectrophotometer. The PAA coated isoplast plate spectrum in the region of 380–430 nm was registered before each deposition of blood. The PAA coated isoplast surface was exposed to 1 ml of each concentration of fresh blood solution. The blood was drawn every 15 seconds and substituted by a fresh blood solution. The spectra obtained for the plate after the exposure to blood were compared with the spectra of blood solutions of 0.5–2.5 mg/ml.

Results

No significant differences were seen in the blood obtained from the different donors. The results presented below were obtained in experiments using blood samples from a single donor.

Five different blood solutions comprising 10, 8, 7, 3.5 and 2.5 mg/ml of blood were tested. For the solutions of a concentration above 2.5 mg/ml, an aggregation and precipitation of blood was observed on the plate surface after 10–30 seconds of exposition (depending on the concentration of the blood solution). An adsorbtion of different sized particles was observed after 60–90 seconds. These particles did not disappear after washing the plate with water or with an HCl solution.

As can be seen in FIGS. 4A–E, 5A–F and 6A–F, the spectra obtained clearly demonstrate a shift of the absorbance band at 386–390 nm and the formation of the peak at 410–412 nm which is typical for hemoglobin solution absorbance. In the experiments whose results are illustrated in FIGS. 6A–F the PAA coated isoplast plates were treated with 0.01 HCl solution (pH=2) prior to the deposition of blood samples. The pretreatment did not prevent the coagulation of blood and even made the changes appear quicker and with better visibility. The absorbance typical for hemoglobin, 412 nm, appeared after a shorter period and the peak was of a better resolution.

In the experiments with blood solutions of 2.5 mg/ml concentration, the visible change in the plate transparency was observed only after 60 seconds.

The results demonstrate that PAA forms a coating on isoplast that is stable at pH=2 and which induces detectable blood coagulation in a period of 30–150 seconds even for blood concentrations as low as 2.5 mg/ml.

Other plastic supports, capable of immobilizing PAA may be used. Plastic supports can also be prepared with a polymethylmetacrylate (PMMA) coating having thrombin linked to the PMMA.

It should be appreciated that since the reaction between the reactant and substance is optically detected, the coating on the support should be homogenous. If other visual information in addition to the information regarding a reaction is expected to be collected, the coating should be transparent in the range of light used for detecting the reaction, as should be the support itself. Any wavelength suitable for detection can be used.

In accordance with an embodiment of the invention there is provided a method for determining in vivo the presence and/or concentration of a biological and/or chemical substance in a body lumen. The method of the invention comprises the steps of: a) inserting into a body lumen a solid support, said support having immobilized thereon at least one reactant capable of reacting with the substance resulting in an optical change and said support being in communication with a detecting unit that is capable of optically detecting a reaction between the reactant and the substance; and b) receiving information from the detecting unit.

The method can be utilized for the detection of substances in body lumens such as blood veins, the gastrointestinal tract or any other internal organ lumen into which a system of the invention can be inserted. Inserting a system for detecting substances in vivo can be accomplished in any appropriate method of insertion such as endoscopy, inserting a needle through the skin or by swallowing.

According to an embodiment of the invention there is provided a diagnostic device for the in vivo detection of substances. The diagnostic device comprises the system of the invention and utilizes the method of the invention.

For example, a system according to the invention can be combined with medical devices such as at the inserted end of an endoscope, stent or needle. The system of the invention can be utilized in a swallowable capsule, such as the swallowable capsule descrtibed in the above mentioned U.S. Pat. No. 5,604,531.

Figure 7:
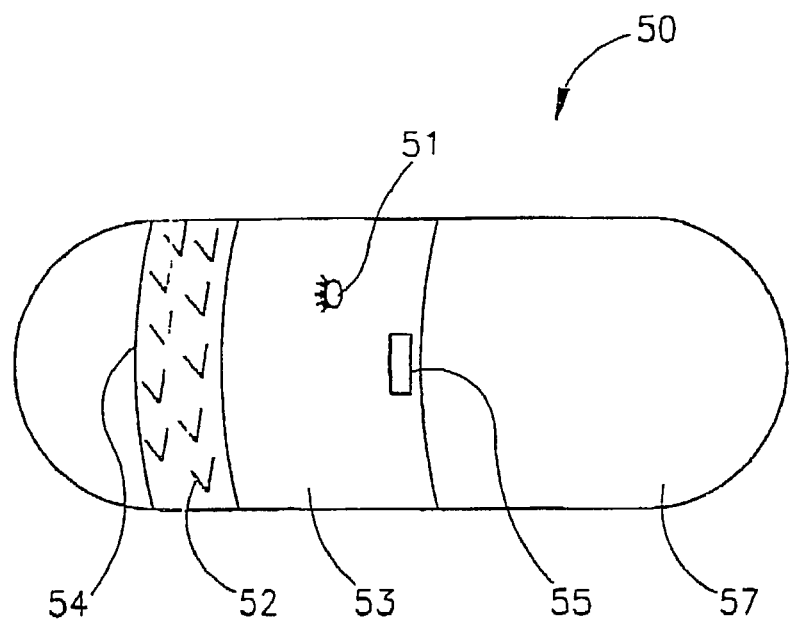
FIG. 7 is a schematic presentation of a diagnostic swallowable kit comprising the system according to the invention.

Reference is now made to FIG. 7 which is a schematic presentation of a swallowable capsule comprising the system of the invention. The swallowable capsule includes a) a camera system, b) an optical system for imaging an area of interest onto the camera system and c) a transmitter which transmits the video output of the camera system. The swallowable capsule can pass through the entire digestive tract and thus, operates as an autonomous video endoscope.

The capsule 50 typically comprises a light source 51, a viewing window 53 through which the light illuminates the inner portions of the digestive system, a camera system 55 such as a charge-coupled device (CCD) camera, which detects the images, an optical system which focuses the images onto the CCD camera system (not shown), a transmitter (not shown) which transmits the video signal of the CCD camera system and a power source 57, such as a battery, which provides power to the entirety of electrical elements of the capsule.

In accordance with the invention any reactant 52 as described above can be immobilized onto the viewing window 53, which is transparent to the illuminating light. The reactant 52 is immobilized as described above to a band 54 on the viewing window 53. The capsule 50 is swallowed or inserted into the gastrointestinal tract and proceeds to passively travel through the length of the tract while the camera 55 images the gastrointestinal tract wall and environment. The images collected from the camera 55 are transmitted and displayed outside of the body.

Figure 8:
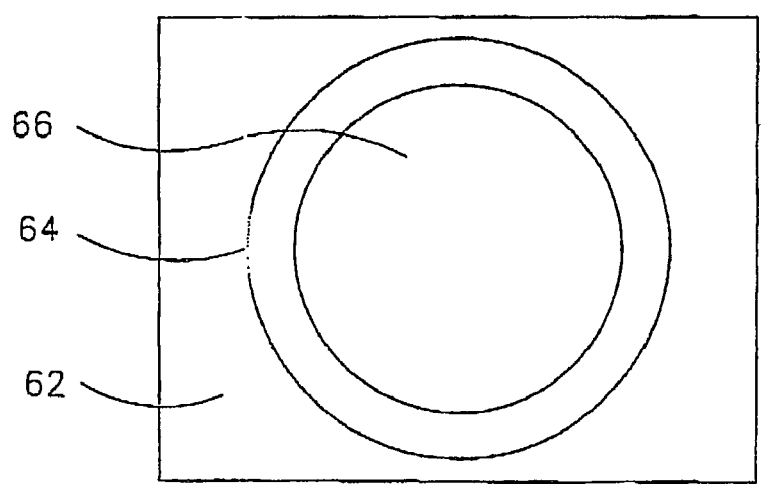
FIG. 8 is a schematic presentation of the picture field displayed by the imaging unit of the device of FIG. 7.

Reference is now made to FIG. 8 which schematically shows the picture field 62 displayed by the camera, such as the image displayed on a physician's work station. Since both the viewing window and the reactant are transparent in the range of light being used, as long as there has been no reaction between the reactant and a substance, direct video images 66 are displayed in the picture field while the reactant band 64 is unnoticed. In the event of a reaction between the reactant and a substance the picture field's 62 optical density or color will be altered only in band 64 in accordance with the reactant used and in accordance with the presence or concentration of the substances in the gastrointestinal tract.

The reactant 52 is stable in a wide range of pH (2–8) surviving the harsh conditions in the stomach and is active through out the GI tract. If there is more than one source of a substance i.e., blood, an accumulation of the substance will augment the reaction, which will be respectively noticed on the picture field 62.

It will be appreciated by persons skilled in the art that the present invention is not limited by what has been particularly shown and described herein above. Rather the scope of the invention is defined by the claims which follow.

The invention claimed is:

1. A system for determining in vivo the presence and/or concentration of a biological and/or chemical substance in a gastrointestinal tract comprising:

an autonomous swallowable capsule comprising:
a light source;
a viewing window through which the light source illuminates the gastrointestinal tract;
a camera system which detects an image of the gastrointestinal tract via the viewing window;
an optical system which focuses the image onto the camera system;
a reactant immobilized on the viewing window which when in the presence of the substance reacts with the substance resulting in an optical change in the image detected by the camera system; and
a battery within the autonomous swallowable capsule to provide power to the camera system and the light source.

2. A system according to claim 1 wherein the viewing window is a glass viewing window.

3. A system according to claim 1 wherein the viewing window is a plastic viewing window.

4. A system according to claim 1 wherein the reactant is immobilized onto the viewing window via a bridging group.

5. A system according to claim 1 wherein the reactant is a chemical compound.

6. A system according to claim 1 wherein the reactant is a biological compound.

7. A system according to claim 1 wherein the reactant is an enzyme.

8. A system according to claim 1 wherein the reactant is an antibody.

9. A system according to claim 1, wherein the camera system is to image the reaction between the reactant and the substance.

10. A system according to claim 1 wherein the reactant is transparent to illumination emitted from the light source.

11. A system according to claim 1 wherein the the cameral system detects optical density.

12. A system according to claim 1 wherein the camera system detects color changes.

13. A system according to claim 1 further comprising a monitoring unit which locates the autonomous swallowable capsule within the gastrointestinal tract.

14. A system according to claim 13 wherein the autonomous swallowable capsule further comprises a transmitting unit which transmits an output of the camera system.

15. A system according to claim 14 wherein the monitoring unit comprises a reception system which receives the transmitted output from the transmitting unit thereby locating the autonomous swallowable capsule along a pre-prepared map of the lumen.

16. A system according to claim 13 wherein the monitoring unit is included within the autonomous swallowable capsule.

17. A system according to claim 1 wherein the combination of the the viewing window and the reactant is transparent to the illumination emitted from the light source.

* * * * *